(12) United States Patent
Anderson et al.

(10) Patent No.: US 12,410,387 B2
(45) Date of Patent: Sep. 9, 2025

(54) PROCESS AND SYSTEM FOR GENERATING HYDROGEN

(71) Applicant: Hydrobe Pty Ltd, Daglish (AU)

(72) Inventors: Duncan Anderson, Daglish (AU); Cristian Coelho Silva, Parana (BR)

(73) Assignee: Hydrobe Pty Ltd, Daglish (AU)

( * ) Notice: Subject to any disclaimer, the term of this patent is extended or adjusted under 35 U.S.C. 154(b) by 451 days.

(21) Appl. No.: 17/482,391

(22) Filed: Sep. 22, 2021

(65) Prior Publication Data

US 2022/0010250 A1 Jan. 13, 2022

Related U.S. Application Data

(63) Continuation of application No. PCT/AU2020/050285, filed on Mar. 25, 2020.

(30) Foreign Application Priority Data

Mar. 25, 2019 (AU) ................................. 2019900999

(51) Int. Cl.
| | |
|---|---|
| *C12N 1/12* | (2006.01) |
| *C12M 1/00* | (2006.01) |
| *C12M 1/107* | (2006.01) |
| *C12P 3/00* | (2006.01) |

(52) U.S. Cl.
CPC ............ *C12M 21/02* (2013.01); *C12M 21/04* (2013.01); *C12M 43/06* (2013.01); *C12M 43/08* (2013.01); *C12N 1/12* (2013.01); *C12P 3/00* (2013.01)

(58) Field of Classification Search
CPC ...... C12M 21/02; C12M 21/04; C12M 43/06; C12M 43/08; C12N 1/12; C12P 3/00
See application file for complete search history.

(56) References Cited

U.S. PATENT DOCUMENTS

| | | |
|---|---|---|
| 2004/0179998 A1 | 9/2004 | Gittleman et al. |
| 2010/0159539 A1* | 6/2010 | Ascon ................... C12M 23/58 435/157 |
| 2013/0157326 A1 | 6/2013 | Oldenburg et al. |

FOREIGN PATENT DOCUMENTS

| | | |
|---|---|---|
| DE | 10059372 A1 | 6/2002 |
| JP | H04334729 A | 11/1992 |
| JP | H0596294 A | 4/1993 |
| JP | 2004057045 A | 2/2004 |
| JP | 2004097116 A | 4/2004 |
| JP | 3544882 B2 | 7/2004 |
| JP | 2004342420 A | 12/2004 |
| KR | 101181834 B1 | 9/2012 |
| KR | 10-20130094866 A | 8/2013 |
| WO | 2013182882 A1 | 12/2013 |

OTHER PUBLICATIONS

Andersson, Viktor. Excess Heat Utilisation in Oil Refineries: CCS and Algae-based Biofuels. Industrial Energy Systems and Technologies, Department of Energy and Environment, Chalmers University of Technology, 2016. (Year: 2016).*
Extended European Search Report dated Dec. 21, 2022 in EP Patent Application No. 20776312.9. 8 pages.
Pachpur, Vinayak Laxman et al.; "Co-culture strategies for increased biohydrogen production"; International Journal of Energy Research; 2015; vol. 39, Issue 11; pp. 1479-1504.
Ghimire, Anish et al.; "Bio-hythane production from microalgae biomass: Key challenges and potential opportunities for algal biorefineries"; Bioresource Technology; 2017; vol. 241; pp. 525-536.
Eroglu, Ela et al.; "Microalgal hydrogen production research"; International Journal of Hydrogen Energy; 2016; vol. 41; pp. 12772-12798.
Obeid, Jamila et al.; "Modelling of hydrogen production in batch cultures of the photosynthetic bacterium *Rhodobacter capsulatus*"; International Journal of Hydrogen Energy; vol. 34, Issue 1; 2009; pp. 180-185.
Kawaguchi, Hideo et al.; "$H_2$ Production from Algal Biomass by a Mixed Culture of *Rhodobium marinum* A-501 and *Lactobacillus amylovorus*"; Journal of Bioscience and Bioengineering; 2001; vol. 91, Issue 3; pp. 277-282.
International Search Report and Written Opinion of the International Searching Authority mailed Jun. 10, 2020 in International Patent Application No. PCT/AU2020/050285. 15 pages.
International Preliminary Report on Patentability mailed Dec. 7, 2020 in International Patent Application No. PCT/AU2020/050285. 83 pages.
Levin, David B. et al.; "Challenges for renewable hydrogen production from biomass"; International Journal of Hydrogen Energy; 2010; vol. 35, Issue 10; pp. 4962-4969.
Cormos, Calin-Cristian; "Assessment of hydrogen and electricity co-production schemes based on gasification process with carbon capture and storage"; International Journal of Hydrogen Energy; 2009; vol. 34, No. 15; pp. 6065-6077.
Navarro, R.M. et al.; "Hydrogen production from renewable sources: biomass and photocatalytic opportunities"; Energy & Environmental Science; 2009: vol. 2, No. 1; pp. 35-54.

(Continued)

*Primary Examiner* — Robert J Yamasaki
*Assistant Examiner* — Trevor Kane
(74) *Attorney, Agent, or Firm* — Kilpatrick Townsend & Stockton LLP

(57) ABSTRACT

Disclosed is a process and system for generating hydrogen from carbon dioxide. The process and system for generating a hydrogen gas stream from a carbon dioxide gas stream comprises converting a first waste carbon dioxide gas stream to an organic feedstock using an algal source in a photosynthesis step. The organic feedstock is then converted using an organism to the hydrogen gas stream and gaseous by-products in a biodecomposition step. The generated hydrogen gas may then be collected.

16 Claims, 11 Drawing Sheets

(56) References Cited

OTHER PUBLICATIONS

Shen, Yafei; "Carbon dioxide bio-fixation and wastewater treatment via algae photochemical synthesis for biofuels production"; RCS Advances; vol. 4, No. 91; pp. 49672-49722.

Redwood, Mark D. et al.; "Integrating dark and light bio-hydrogen production strategies: towards the hydrogen economy"; Reviews in Environmental Science and Bio/Technology; 2009; vol. 8, No. 149; pp. 1-45 (p. 45 is blank).

English translation of Office Action mailed Sep. 27, 2022 in JP Patent Application No. 2021-560170. 7 pages.

Lage, Sandra et al.; "Algal Biomass from Wastewater and Flue Gases as a Source of Bioenergy": 2018; Energies; vol. 11, No. 3; 664; doi:10.3390/en11030664; 30 pages.

English translation of Office Action mailed Jun. 26, 2023 in KR Patent Application No. 10-2021-7034421. 6 pages.

Office Action mailed Aug. 9, 2023 in CN Patent Application No. 202080035464.X with English machine translation. 19 pages.

Office Action mailed Feb. 9, 2024 in CN Patent Application No. 202080035464.X with English machine translation. 16 pages.

Wang, Quan et al.; "Effective lipid extraction from undewatered microalgae liquid using subcritical dimethyl ether"; Biotechnology for Biofuels; 2021; vol. 14, No. 17; https://doi.org/10.1186/s13068-020-01871-0; 13 total pages.

Tzima, Soulana et al.; "Recent Advances in Supercritical $CO_2$ Extraction of Pigments, Lipids and Bioactive Compounds from Microalgae"; Molecules; 2023; vol. 28, No. 3; https://doi.org/10.3390/molecules28031410; 61 total pages.

Weber, Sophie et al.; "Insights into cell wall disintegration of *Chlorella vulgaris*"; Plos One; Published: Jan. 14, 2022; vol. 17, No. 1; https://doi.org/10.1371/journal.pone.0262500; 14 total pages.

Maltsev, Yevhen et al.; "Nitrogen and phosphorus stress as a tool to induce lipid production in microalgae"; Microbial Cell Factories; 2023; vol. 22, No. 239; https://doi.org/10.1186/s12934-023-02244-6; 22 total pages.

Gerken, Henri G. et al.; "Enzymatic cell wall degradation of *Chlorella vulgaris* and other microalgae for biofuels production"; Planta; 2013; vol. 237; https://doi.org/10.1007/s00425-012-1765-0; pp. 239-253.

Davis, Ryan et al.; "Techno-economic analysis of autotrophic microalgae for fuel production"; Applied Energy; Oct. 2011; vol. 88, No. 10; https://doi.org/10.1016/j.apenergy.2011.04.018; pp. 3524-3531.

\* cited by examiner

PROCESS AND SYSTEM FOR GENERATING HYDROGEN

CROSS-REFERENCES TO RELATED APPLICATIONS

This application is a continuation application of International Patent Application No. PCT/AU2020/050285 entitled "PROCESS AND SYSTEM FOR GENERATING HYDROGEN," filed on Mar. 25, 2020, which claims priority to Australian Patent Application No. 2019900999, filed on Mar. 25, 2019, each of which are herein incorporated by reference in their entirety for all purposes.

TECHNICAL FIELD

This disclosure relates to the conversion of carbon dioxide to hydrogen using bioreactors.

BACKGROUND OF THE INVENTION

Lithium and hydrogen technologies are competing to determine the future of electric vehicles. The constraints of lithium are vehicle range and time to recharge, and the challenges associated with hydrogen are the high cost of fuel, transport and storage.

Both technologies are ostensibly 'green' in that the operating vehicle does not emit carbon dioxide. However, both hydrogen and lithium fueled electric vehicles require a fuel source that at some point contributes to greenhouse gas emissions.

Lithium batteries have become the dominant technology in the electric vehicle industry. Notwithstanding, the traditional internal combustion engine remains more cost effective and convenient, particularly for long haul transit. Accordingly, and regardless of the technology, electric vehicles remain a niche and not yet in a position to fully disrupt the auto vehicle market. With many of the World's leading nations looking to phase out internal combustion engines in the medium term, the potential for cost effective fuel cell technology is massive. With the current price of production for hydrogen being too high to support larger scale use in electric vehicles, there is a need to provide hydrogen at more cost-effective levels.

In this regard, the "pump" price of hydrogen must be comparable with petrol for hydrogen vehicles to become more mainstream. For example, a TOYOTA MIRAI™ uses approximately 5 kilograms of hydrogen to travel 500 kilometres. An equivalent petrol-powered passenger vehicle uses approximately 40 litres of petrol to cover the same distance. Assuming a petrol price in the range of USD $1.00 to $1.25 per litre, the cost of that trip is between US$40-US$50. For the hydrogen fueled TOYOTA MIRAI™ to be price competitive over the same distance, the retail price of hydrogen needs to be between US$8 and US$10 per kilogramme. However, such prices of hydrogen are not yet available for the consumer.

An issue with current hydrogen production is that the majority (i.e. >90%) of hydrogen is derived from hydrocarbons. Migration to a hydrogen economy where the hydrogen is produced from hydrocarbons will do little to mitigate the effects of greenhouse gas production.

Another way to generate hydrogen is through electrolytic splitting of water. However, water splitting is not viable long term for a number of reasons. For example, to achieve hydrogen production rates of 500 kg per day, large scale equipment is required, real estate availability is challenging, and capital costs are very expensive. The energy requirement is high per unit of hydrogen produced, which can be offset by using solar energy, but the use of solar energy is only available during daylight hours and can be irregular. Therefore, substantial buffer storage is required to deliver a viable solution which adds to capital cost. The overall yield of hydrogen production from water splitting is physically constrained and unlikely to reach a level where the unit cost (including capital recovery) will ever fall below the target price.

Hydrogen can also be produced through steam reforming methane (grid gas) on site. Steam reforming requires temperatures of 700° C.-1000° C. and is energy intensive. Hydrogen yields for steam reforming are much higher than water splitting. However, small-scale steam reforming plants that use grid gas face problems. Grid gas contains a mix of methane, butane and ethane gasses where only methane is typically used for steam reforming, and grid gas at retail sites is generally more expensive than methane at a liquified natural gas (LNG) production facility. Steam reforming also generates about 9 kg of carbon dioxide for every kg of hydrogen produced. Without carbon capture and storage solutions, steam reforming is environmentally unviable when looking to move to a hydrogen economy.

Direct conversion of methane and other hydrocarbons to pure hydrogen with microbes remains a challenge on a large scale where efficiency is a determining factor. For example, bacterial species such as *Caldicellulosiruptor saccharolyticus* are known to convert methane from rotting organic matter into hydrogen. However, this direct conversion is not as efficient as converting methane from grid gas into hydrogen by steam reforming. Further, without the surrounding biomass, carbon dioxide production will remain an unsolved problem for bacterial conversion of grid gas into hydrogen.

Hybrid systems involving traditional chemical process (steam reforming) can also be used to generate hydrogen. In these hybrid systems the carbon dioxide generated during steam reforming is captured and processed into organic components for disposal using microbial algae. However, hybrid systems do not mitigate the issue of carbon dioxide production, although they do provide a lower cost carbon storage solution, and they also do not solve the cost equation for smaller scale steam reforming of grid gas.

It is to be understood that, for any prior art publication or reference that is referred to herein, such reference does not constitute an admission that the publication forms a part of the common general knowledge in the art, in Australia or any other country.

BRIEF SUMMARY OF THE INVENTION

A first aspect of the disclosure provides a process for generating a hydrogen gas stream from a carbon dioxide gas stream. The process comprises: (i) converting a first waste carbon dioxide gas stream to an organic feedstock using an algal source in a photosynthesis step. The process also comprises: (ii) converting the organic feedstock, using an organism, to the hydrogen gas stream and gaseous by-products in a biodecomposition step that includes an aerobic biodecomposition step and an anaerobic biodecomposition step. An embodiment may further comprise collecting the hydrogen gas stream.

The term "algal source" as used herein is to mean one or more algal species capable of photosynthetically converting carbon dioxide into an organic feedstock. The term "organic feedstock" as used herein is to mean a feedstock having organic matter, such as biomass, that can include simple and complex carbohydrates, such as simple and complex sugars, biopolymers such as exopolysaccharides, algal debris and by-products from photosynthesis. The organic feedstock can also include material used during the photosynthesis step, such as materials and reagents present in a culture medium that is used for the photosynthetic conversion of carbon dioxide into the organic feedstock. The term "biodecomposition" as used herein is to mean conversion of the organic feedstock into other forms, including hydrogen gas, using one or more organisms in one or more biological processes.

The carbon dioxide gas stream may be generated by combustion of hydrocarbons, such as in a coal- or gas-fired power station, or conversion of hydrocarbons into other gases that include carbon dioxide, such as occurs with steam reforming. The disclosed process may provide an efficiency saving by counterintuitively breaking the conversion of e.g. methane (i.e. hydrocarbons) to hydrogen into two separate steps. An advantage of the disclosed process can be that waste carbon dioxide, such as that generated by industrial processes, may be converted into hydrogen. Therefore, the process may be used as a way to "scrub" or remove carbon dioxide from the atmosphere or from carbon dioxide producing activities. The disclosed process may be used in place of carbon dioxide sequestration such as where carbon dioxide is pumped and stored in geological formations. An added advantage of the disclosed process compared to existing carbon dioxide sequestration techniques can be that the present process also produces hydrogen gas as a renewable gas source.

The process may further comprise collecting gaseous by-products and filtering the gaseous by-products to isolate a second waste carbon dioxide gas stream. The process may further comprise transferring the second waste carbon dioxide stream to step (i). The first and second waste carbon dioxide gas streams may be combined. In an embodiment, step (i) may be performed in a microbial reactor that is fitted with a photon source. The algal source may include algae in the class Chlorophyceae and/or Trebouxiophyceae. The algal source may be a chlorophyte. The algal species may be part of the *Chlorella* genus. In an embodiment the algal species may be *Chlorella vulgaris*.

Step (ii) may include an aerobic biodecomposition step and an anaerobic biodecomposition step. The aerobic biodecomposition step may be performed before the anaerobic biodecomposition step. In an embodiment, at least a portion of a product of the aerobic biodecomposition step may be mixed, such as recirculated, with the algal source in step (i) prior to passing the mass to the anaerobic biodecomposition step. In an embodiment, the mixing of the at least a portion of the product of the aerobic biodecomposition step with the algal source in step (i) acts as a collective 'feed production stage' for the anaerobic biodecomposition step.

In an embodiment, step (ii) may be performed in one or more biodecomposition reactors. For example, each biodecomposition reactor may include an aerobic reactor and an anaerobic reactor. The biodecomposition reactor may comprise one or more bacterial species. The bacterial species may be in the class Clostridia, Gamma Proteobacteria, Bacilli, Cocci and/or Betaproteobacteria. The bacterial species may be Gram-positive and/or a catalase-positive bacterium. The bacterial species may include Gram-negative bacteria. The bacterial species may be part of the genus *Bacillus*. In an embodiment, the bacterial species may include *Bacillus subtilis*. The bacterial species may be part of the class Gammaproteobacteria. The bacterial species may be part of the genus *Klebsiella*. In an embodiment, the aerobic biodecomposition reactor may include Gammaproteobacteria and the anaerobic biodecomposition reactor may include *Enterobacter aerogenes* (currently classified as *Klebsiella aerogenes*).

The process may further comprise regulating a temperature of step (i) and/or step (ii), such as with a heat source. For example, steps (i) and (ii) may both be maintained at about 35° C. The specific temperature of the photosynthesis step and/or the biodecomposition step may be determined by and regulated so as to favour the algal source and/or bacteria used in these steps.

The first waste carbon dioxide gas stream may be generated from a gas reforming step (e.g. by a steam reformer) that forms a secondary hydrogen gas stream from a hydrocarbon source. The heat source for regulating the temperature of step (i) and/or step (ii) may be provided from heat generated from the steam reformer. The hydrocarbon source may be natural gas, such as methane.

A gas reformer generates hydrogen and carbon dioxide. When the first waste carbon dioxide gas stream is formed by a gas reformer, the disclosed process may be used to supplement the hydrogen generated by the gas reformer (i.e. to provide a secondary hydrogen gas stream). When a gas reformer is used, the production of hydrogen gas from the gas reformer may be increased from 40% to 65% per unit volume of natural gas consumed by using at least some embodiments of the disclosure.

The process may further comprise filtering the gaseous by-products to isolate a waste hydrocarbon gas stream. The waste hydrocarbon gas stream may be used to supplement the hydrocarbon source. In an embodiment, the hydrogen gas stream and the secondary hydrogen gas stream may be combined. The secondary hydrogen gas stream may produce a greater volume of hydrogen gas compared to the (primary) hydrogen gas stream. The process may further comprise supplying water to step (i).

The process may further comprise collecting organic-rich matter from step (ii). The organic-rich matter can be the by-product of the biodecomposition step of converting the organic feedstock into hydrogen. The organic-rich matter may be used as a bio-fertilizer. In an embodiment, the process can be used to convert any carbon dioxide source into methane, hydrogen and bio-fertilizer.

Disclosed is a process for generating a hydrogen gas stream from a carbon dioxide gas stream. The process comprises (i) mixing a first waste carbon dioxide gas stream and an algal source to form an organic feedstock. The process also comprises (ii) treating the organic feedstock in a first biodecomposition step to produce a first biodecomposition product. The process further comprises (iii) treating the first biodecomposition product in a second biodecomposition step to produce hydrogen gas; wherein, prior to step (iii), at least a portion of the first biodecomposition product is mixed with the algal source in step (i). In an embodiment, the first biodecomposition step may be aerobic and the second biodecomposition step may be anaerobic. When the first biodecomposition step is aerobic, the combination of the first biodecomposition step and the algal source can be considered as a collective 'feed production stage' for the anaerobic biodecomposition step. In an embodiment, the process may be as otherwise as set forth above.

Without being bound by theory, it is thought that mixing at least a portion of the first biodecomposition product with the algal source helps to enable (i) a higher carbon dioxide concentration by increasing glucose production, and (ii) increase hydrogen production by preparing the biomass, including pH for more efficient bio-processing in the second biodecomposition reactor. An embodiment may allow refined biomass and glucose generated in the first biodecomposition step to be recirculated between aerobic bacteria the first biodecomposition step and aerobic algae in step (i). Instead of producing hydrogen, by transferring at least a portion of the first biodecomposition product and mixing it with the algal source in step (i), compounds other than hydrogen may be generated, such as methanol and other alcohols. Organisms that are used to produce hydrogen may be different to those that are used generate other products such as alcohol(s).

An embodiment of the process may eliminate carbon dioxide emissions, reduce the energy cost per kilogram of hydrogen produced, and increase the hydrogen units generated per unit of natural gas consumed.

The disclosure also provides hydrogen generated using the process as set forth above.

The disclosure also provides organic matter produced from the process as set forth above.

Also disclosed is a process for sequestering carbon dioxide from a gas stream that comprises carbon dioxide. The process comprises converting the carbon dioxide in the gas stream to an organic feedstock using an algal source in a photosynthesis step. The process also comprises converting the organic feedstock, using an organism, to a refined biomass in an aerobic biodecomposition step.

Also disclosed is a process for increasing the production of glucose from a carbon dioxide gas stream. The process comprises converting the carbon dioxide gas stream to an organic feedstock using an algal source in a photosynthesis step, the feedstock including glucose. The process also comprises subjecting the organic feedstock including the glucose to an aerobic biodecomposition step to produce a biomass. In the process a portion of the biomass produced in the aerobic biodecomposition step is recirculated to the algal photosynthesis step to thereby increase the production of glucose in the organic feedstock.

The disclosure also provides a method of generating electricity, comprising: generating a hydrogen gas stream as set forth above and using the hydrogen gas stream as a fuel source in an electrical generation step.

The electrical generation step may include passing the hydrogen gas through a fuel cell to thereby generate electricity. The electrical generation step may include enriching a combustible fuel with the hydrogen to form a hydrogen-enriched fuel. The hydrogen-enriched fuel may be combusted to drive an electric generator. The first waste carbon dioxide gas stream may be generated from a coal- or gas-fired power station.

The disclosure also provides a system for generating a hydrogen gas stream from a carbon dioxide gas stream. The system comprises a photosynthesis reactor configured to convert a first waste carbon dioxide gas stream into an organic feedstock using an algal source, the photosynthesis reactor having an inlet for receiving a carbon dioxide gas stream and an organic feedstock outlet. The system also comprises a biodecomposition reactor comprising an inlet in communication with the organic feedstock outlet for receiving the organic feedstock, the biodecomposition reactor configured as an aerobic biodecomposition reactor and as an anaerobic biodecomposition reactor to convert the organic feedstock from the photosynthesis reactor into the hydrogen gas stream.

The system may further comprise a hydrogen storage vessel in fluid communication with the biodecomposition reactor for receiving and storing the hydrogen gas stream generated in the biodecomposition reactor. The system may further comprise an auxiliary carbon dioxide supply line for transferring carbon dioxide generated in the biodecomposition reactor to the photosynthesis reactor. The auxiliary carbon dioxide supply line may comprise a filter for filtering gases other than carbon dioxide. The system may further comprise one or more heat exchangers to heat each of the photosynthesis reactor and biodecomposition reactor.

In an embodiment the system may further comprise a gas reformer for converting a hydrocarbon into a second hydrogen gas stream and the first waste carbon dioxide gas stream. The second hydrogen gas stream may be in fluid communication with the hydrogen storage vessel. The first waste carbon dioxide gas stream may be in fluid communication with the photosynthesis reactor. The one or more heat exchangers may be configured to transfer heat generated by the gas reformer to the photosynthesis reactor and/or to the biodecomposition reactor.

In an embodiment, the system may further comprise an auxiliary hydrocarbon feed line connecting the biodecomposition reactor with the gas reformer for transferring hydrocarbons generated by the biodecomposition reactor to the gas reformer. The auxiliary hydrocarbon supply line may comprise a filter for filtering of gases other than hydrocarbons.

The system may further comprise a combustion chamber in fluid communication with and upstream of the photosynthesis reactor. The combustion chamber may be configured to combust a fuel source to generate the first waste carbon dioxide gas stream.

The photosynthesis reactor and/or the biodecomposition reactor may be provided on a transportable structure, for example in a standard shipping container. The photosynthesis reactor and/or the biodecomposition reactor may each be provided as modular units. Scaling the system up or down may be achieved by adding or subtracting appropriate units. The system may further comprise a water supply, for example in fluid communication with the photosynthesis reactor and/or biodecomposition reactor. The photosynthesis reactor and/or the biodecomposition reactor may comprise a plurality of reactors. The plurality of reactors may be arranged in series or parallel with one another.

In an embodiment, the system may further comprise a photosynthesis antifoamer configured to prevent foaming in the photosynthesis reactor and/or a biodecomposition antifoamer configured to prevent foaming in the biodecomposition reactor. The system may be provided with a recirculator for recirculating water and/or biomass between the photosynthesis reactor and the biodecomposition reactor. The recirculator may transport materials and nutrients around the system, for example to support the algal and/or bacterial communities in the photosynthetic reactor and/or biodecomposition reactor. The water used in the recirculator may be used as a transport medium for transporting matter around the system.

The system may further comprise a controller for controlling the photosynthesis reactor and/or the biodecomposition reactor. The system may further comprise an air supply for supplying air to the biodecomposition reactor. The air supply may include a biological filter for filtering biological matter from the air that is supplied by the air supply to the biodecomposition reactor. Water from a water source may be supplied to the photosynthetic reactor.

In an embodiment, the disclosure also provides use of a system as set forth above to generate hydrogen.

In an embodiment, the disclosure also provides a hydrogen vehicle refuelling station comprising the system as set forth above.

BRIEF DESCRIPTION OF THE DRAWINGS

Embodiments will now be described with reference to the accompanying non-limiting Figures, by way of example only.

DETAILED DESCRIPTION OF THE INVENTION

Figure 1:
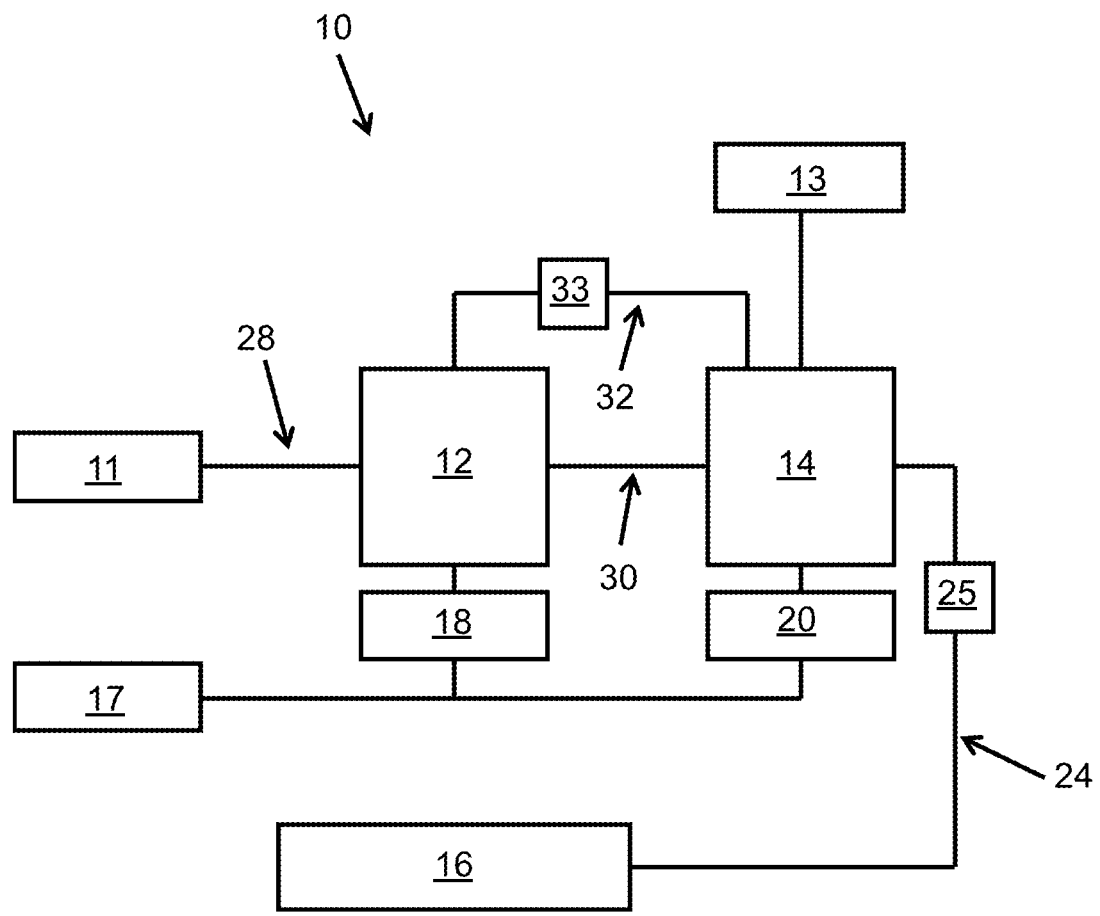
FIG. 1 shows a schematic of a system used to generate hydrogen in accordance with an embodiment of the disclosure.

An embodiment of a system 10 used for the production of hydrogen is shown in FIG. 1. System 10 has a microbial reactor in the form of photobioreactor 12 that is configured to convert carbon dioxide into an organic feedstock using photosynthesis. The organic feedstock includes simple and complex carbohydrates, such as simple and complex sugars, and biopolymers such as exopolysaccharides. In an embodiment, the organic feedstock produced by the photobioreactor 12 includes biomass and sugars derived from glucose and polysaccharides. In an embodiment, the organic feedstock includes a mixture of different carbohydrates. The system 10 also has a carbon dioxide supply line 28 that feeds carbon dioxide from a carbon dioxide source 11 into the photobioreactor reactor 12. The carbon dioxide supply line 28 may include a filter to filter off gases other than carbon dioxide. The system 10 also includes a biodecomposition reactor 14.

The carbon dioxide delivered to the photobioreactor 12 may be mixed with other gases, such as air. In an embodiment, a concentration of the carbon dioxide delivered to the photobioreactor 12 ranges up to about 50%. In an embodiment, a concentration of the carbon dioxide delivered to the photobioreactor 12 ranges from about 8% to about 20%. Carbon dioxide may be supplied to the photobioreactor 12 at a rate of about 0.2 to about 0.8 VVM. In an embodiment, a mixing manifold is provided (not shown in the Figures) to allow a concentration of carbon dioxide in the waste carbon dioxide gas stream to be adjusted.

The photobioreactor 12 and biodecomposition reactor 14 are connected to one another via a conduit 30. The conduit 30 passes the organic feedstock from an organic feedstock outlet of the photobioreactor 12 to an inlet of the biodecomposition reactor 14. The organic feedstock is provided as a solid, slurry and/or liquid. In an embodiment, the organic feedstock is provided as a solution that is fed to the biodecomposition reactor 14. In an embodiment, the conduit 30 has a pump or auger for pumping or conveying the organic feedstock from the photobioreactor 12 to the biodecomposition reactor 14. The biodecomposition reactor 14 is set up to convert the organic feedstock into hydrogen. In an embodiment a filter is provided at the photobioreactor 12 so that only the organic feedstock is passed from the photobioreactor 12 to the biodecomposition reactor 14. In an embodiment, only a portion of the organic feedstock generated in the photobioreactor 12 is transferred to the biodecomposition reactor 14. For example, a portion of the organic feedstock is kept as an inoculum. In an embodiment, 60% of the organic feedstock produced in the photobioreactor 12 is transferred to the biodecomposition reactor 14 and 40% of the organic feedstock is retained as an inoculum for further use in the photobioreactor 12. The reactors 12 and 14 can be operated as batch, semi-batch or continuous processes.

The hydrogen generated in the biodecomposition reactor 14 is transferred via a conduit 24 to a hydrogen storage vessel in the form of storage vessel (e.g. tank) 16. Conduit 24 includes a pump 25 to pump the generated hydrogen to the storage vessel 16. The pump 25 can allow the storage vessel 16 to be pressurised. However, the pump 25 is not required in all embodiments. It should be appreciated that the term "storage vessel" is to be interpreted broadly to include any form of closed/closeable vessel that is capable of storing hydrogen and also includes materials that can adsorb (i.e. reversibly adsorb) hydrogen such as carbonaceous materials, metal-organic frameworks and molecular sieves.

The required hydrogen output determines the required output of the photobioreactor 12. The required output of the photobioreactor 12 will be dependent on the required input rate of the organic feedstock to the biodecomposition reactor 14.

The photobioreactor 12 is configured for the photosynthetic conversion of carbon dioxide into an organic feedstock. The specific reaction conditions of the photobioreactor 12 are dependent on the biochemical requirements for the organisms present in the photobioreactor 12. However, the organisms present in the photobioreactor 12 are generally phototrophic. The phototrophic organisms can include algal species and mosses, and phototrophic bacteria such as cyanobacteria and purple bacteria. It should be appreciated that cyanobacteria are sometimes considered to be an algal species, and are referred to as such in this disclosure. In an embodiment, the photobioreactor includes algae of the class Chlorophyceae and/or Trebouxiophyceae. Cyanophyceae can include cyanobacteria and blue-green algae. In an embodiment, Chlorophyceae includes *Acutodesmus obliquus, Scenedesmus subspicatus, Dunaliella salina* and/or *Scenedesmus obliquus*. In an embodiment, Trebouxiophyceae includes *Chlorella vulgaris*.

The specific time required to generate the organic feedstock may be dependent upon a cell concentration and the algal species used as the inoculum in the photobioreactor 12. When an algal species concentration threshold is reached, this can represent the trigger for the resulting organic feedstock to be transferred to the biodecomposition reactor. For example, in an embodiment, the organic feedstock is transferred from the photobioreactor 12 to the biodecomposition reactor 14 when a density of the algal species is approximately $2\times10^7$ to approximately $2\times10^9$ CFU/ml. In an embodiment, the photobioreactor 12 is operated for 48 hours to produce the organic feedstock. After 24 hours the organic feedstock may have an algal species density of $2\times10^7$ CFU/ml. It should be noted that the time to reach the final max cell density cell density may be dependent on the inoculum cell concentration used to initially seed the photobioreactor 12.

The composition of the media used in the photobioreactor 12 will be dependent upon the phototrophic organism. Parameters such as media, pH, salinity, nutrient requirements, required light dosage rates, photosynthesis temperature, and so on will be adjusted according to requirements of the phototrophic organism. Generally, the temperature of the photosynthesis conversion of carbon dioxide into the organic feedstock that is performed in the photobioreactor 12 will range from about 30° C. to about 40° C. The type of phototrophic organism used, and the resulting organic feedstock produced by the phototrophic organism, may be selected depending upon the requirements of the biodecomposition reactor 14. In an embodiment more than one type of phototrophic organism is used in the photobioreactor 12. Throughout this disclosure the use of the term "phototropic organism" includes mixtures of two or more specific phototrophic organisms.

The phototrophic organism may be provided as a concentrate solution that is transferred into the photobioreactor 12 and allowed to proliferate. In an embodiment, the phototrophic organism may be provided in a dehydrated form that is rehydrated in the photobioreactor 12. The photobioreactor 12 may require periodic cleaning whereby the media and phototrophic organism are replaced with a fresh batch of media and phototrophic organism. Unwanted by-products such as biofilms may be removed at this time. During conversion of carbon dioxide into sugars, biomass is also produced.

The biodecomposition step that is performed in the biodecomposition reactor 14 converts the organic feedstock generated in the photobioreactor 12 into hydrogen. The specific mechanism and biochemical requirements of the biodecomposition step are dependent upon the organism(s) present in the biodecomposition reactor 14 and the type of organic feedstock produced by the photobioreactor 12. For example, in an embodiment, fermentation processes are used to convert the organic feedstock into hydrogen in biodecomposition reactor 14. In an embodiment, the biodecomposition reactor 14 is operated under anaerobic and/or aerobic conditions. In an embodiment, the amount of hydrogen produced in the biodecomposition reactor 14 is 41 mol % based on glucose equivalents in the organic feedstock.

Based on a photobioreactor with a volume of 0.5 L, in an embodiment, 5.04 grams per 24 hours of hydrogen gas, 32.06 grams of carbon dioxide and 18.49 grams of methane is produced using system 10. In an embodiment, about 10.08 grams of hydrogen may be produced from 1 L of organic feedstock that is produced in the photobioreactor 12. This 0.5 L photobioreactor can be scaled up or scaled out depending on the required hydrogen output. Based on a photobioreactor 12 with a volume of 0.5 L, the mass-balance for inputs and outputs is provided in Table 1. Surprisingly, the conversion of carbon dioxide to hydrogen proceeded with an efficiency of 64.3 mol % based off the amount of carbon dioxide input, which is 4-5 times higher than that based on known literature values.

TABLE 1

| Inputs | | | | | | Outputs | | | | | | |
|---|---|---|---|---|---|---|---|---|---|---|---|---|
| Component | Kmol/Hr | Mol weight | KG/Hr | KG/Day | Input ratio | Component | Kmol/Hr | Mol weight | KG/Hr | KG/Day | Wt ratio vs $CO_2$ | Mol ratio vs mol ($CO_2$) input |
| $CO_2$ | 1.62E−04 | 44.0 | 7.13E−03 | 1.71E−01 | 14% | $H_2$ | 1.04E−04 | 2.01 | 2.10E−04 | 5.04E−03 | 2.9% | 64.3% |
| $H_2O$ | 2.78E−02 | 18.0 | 5.01E−01 | 5.01E−01 | 42% | $CH_4$ | 4.80E−05 | 16.0 | 7.70E−04 | 1.85E−02 | 11% | 29.6% |
| air | — | — | 2.21E−02 | 5.29E−01 | 44% | $CO_2$ | 3.04E−05 | 44.0 | 1.34E−03 | 3.21E−02 | 19% | 6.03% |

In an embodiment, following the photosynthesis step in the photobioreactor 12, water acts as a transport medium to transport the organic feedstock (e.g. sugars and biomass) from the photobioreactor 12 to the biodecomposition reactor 14. The use of water as a transport medium helps to distribute the carbon dioxide and nutrients in the photobioreactor 12. In an embodiment, the water transport medium is recirculated around the system 10 and carbon dioxide in the system 10 can be mixed (e.g. emulsified) and recirculated between the photobioreactor 12 and the biodecomposition reactor 14 until the carbon dioxide is converted into organic material or hydrogen. Similarly, some of the products formed in the biodecomposition reactor 14 can be recirculated around system 10. The water transport medium may be filtered to filter off water-soluble gas(es) produced during use of the system 10. The term "water transport medium" is to be interpreted broadly to include any aqueous-based solution. For example, the water transport medium can include reaction media, salts, buffers, nutrients, additives to promote favourable gas absorption, and so on.

Bacteria used in the biodecomposition reactor 14 may belong to the Thermoanaerobacterales order. Thermoanaerobacterales bacteria may include *Thermotoga maritima, Caldicellulosiruptor saccharolyticus* and *Thermotoga elfii*, although these bacteria are exemplary only and do not limit the scope of this disclosure. In an embodiment, the bacteria used in the biodecomposition reactor 14 is of the Clostridia class. The Clostridia class may include *Thermotoga maritima, Caldicellulosiruptor saccharolyticus*, and/or *Thermotoga elfii*. In an embodiment, the bacteria used in the biodecomposition reactor 14 is of the Gamma Proteobacteria class. The Gamma Proteobacteria class may include *Escherichia coli* and *Pseudomonas syringae*. In an embodiment, the bacteria used in the biodecomposition reactor 14 is of the Bacilli class. The Bacilli class may include *Bacillus licheniformis, Bacillus amyloliquefaciens, Bacillus subtilis* and/or *Bacillus atrophaeus*. In an embodiment, the bacteria used in the biodecomposition reactor 14 is of the Cocci class. The Cocci class may include non-pathogenic variants of *Staphylococcus warneri*. In an embodiment, the bacteria used in the biodecomposition reactor 14 is of the Betaproteobacteria class. A combination of bacteria may be used in the biodecomposition reactor 14, for example various combinations of bacteria in the Clostridia, Gamma Proteobacteria, Bacilli, Cocci and/or Betaproteobacteria class. The clostridia class may include *Caldicellulosiruptor saccharolyticus*. The biodecomposition reactor 14 may also include root nodule bacteria.

In an embodiment, the bacteria used in the biodecomposition reactor 14 uses the sugars produced in the photobioreactor 12 as a food source and also extract the sugars within associated biomass without mechanical or chemical intervention. A water transport mechanism is used to facilitate the transfer of sugars and biomass produced in the photobioreactor 12 into the biodecomposition reactor 14. An advantage of using bacteria that use the sugars produced in the photobioreactor 12 as a food source, and that extract the sugars within associated biomass without mechanical or chemical intervention, is that the biodecomposition reactor 14 may provide an energy saving because less equipment and/or processes are required to generate hydrogen.

In an embodiment, additional feedstocks, such as raw biomass sources and water, may be added to the biodecomposition reactor 14 to facilitate the production of hydrogen. Biomass may be removed from the system when the photobioreactor 12 and/or biodecomposition reactor 14 are flushed. The photobioreactor 12 and biodecomposition reactor 14 may be flushed at the same time or at different times. Flushing of the photobioreactor 12 and/or biodecomposition reactor 14 allows fresh inoculum to be introduced into the photobioreactor 12 and/or biodecomposition reactor 14.

In an embodiment, the photobioreactor 12 has an algal concentration of about $2 \times 10^{11}$ cells per ml, and the biodecomposition reactor 14 has a bacterial concentration of about $1.5 \times 10^{10}$ cells per ml. In an embodiment, the photobioreactor 12 and/or the biodecomposition reactor 14 may be operated at a pressure ranging from 1 atm to 5 atm.

The biodecomposition reactor 14 includes an outlet for extracting organic-rich matter generated during the conversion of the organic feedstock to hydrogen (not shown in the Figures). The outlet for the organic-rich material can be an underflow from reactor 14. The organic-rich material may be used as a bio-fertilizer and sold as a separate feedstock. Revenue generated from the separate feedstock may be used to supplement the operational costs of the system 10. In an embodiment, the organic-rich material is extracted when system 10 is renewed or purged with new species in the photobioreactor 12 and/or biodecomposition reactor 14, with the extracted matter being the organic-rich material. In an embodiment, the organic-rich material can provide a biofertilizer. The organic-rich material extracted from the system 10 is then replaced with new inoculation of species in the photobioreactor 12 and biodecomposition reactor 14, such as microalgae and bacteria. Extraction of the organic-rich material can occur periodically, such as approximately every two to three weeks.

In an embodiment, the organic-rich material has the following composition:
Potassium: 2.67%
Calcium: 4.77%
Magnesium: 0.74%
Copper: 20.26 ppm
Manganese: 309.52 ppm
Iron: 1 ppm
Zinc: 80 ppm
Aluminum: 1%
Sulfur: 0.5%
Sodium: 2%
Boron: 0.008%
Organic Carbon: 23.3%
Carbon/Nitrogen Ratio: 24:1
Humidity (65° C.) 90%
Organic matter: 10%
Nitrogen Total: 0.96%
Density: 1.1 g/cm$^3$ In use, the biodecomposition reactor 14 generates hydrogen and waste carbon dioxide and/or waste hydrocarbons. The relative amounts of hydrogen, carbon dioxide and hydrocarbons generated in the biodecomposition reactor 14 generally depends on the biodecomposition reactor conditions. Because the photobioreactor 12 uses carbon dioxide as a feedstock, the biodecomposition reactor 14 can be fitted with an auxiliary carbon dioxide supply line 32 that transfers any carbon dioxide generated by the biodecomposition reactor 14 to the photobioreactor 12 (i.e. a carbon dioxide recycle line). This means that carbon dioxide generated by the biodecomposition reactor 14 can be used as a feedstock for the photobioreactor 12. The auxiliary carbon dioxide supply line 32 can help improve the efficiency of the system 10 as a greater hydrogen yield can be achieved per unit of carbon dioxide delivered to the system by carbon dioxide supply line 28.

The auxiliary carbon dioxide supply line 32 can be connected to the biodecomposition reactor 14 or alternatively the auxiliary carbon dioxide supply line 32 can branch off conduit 24. In either configuration, the auxiliary carbon dioxide supply line 32 is fitted with a filter 33, such as a membrane filter, for filtering the carbon dioxide gas from other gases e.g. hydrogen and hydrocarbons.

A photosynthesis heat exchanger 18 is in thermal communication with the photobioreactor 12 and a biodecomposition heat exchanger 20 is in thermal communication with the biodecomposition reactor 14. The heat exchangers 18 and 20 are connected to heat source 17 to supply heat to the reactors 12 and 14. In FIG. 1, the heat exchangers 18 and 20 are connected in parallel to the heat source 17, but the heat exchangers 18 and 20 may optionally be connected in series.

Figure 2:
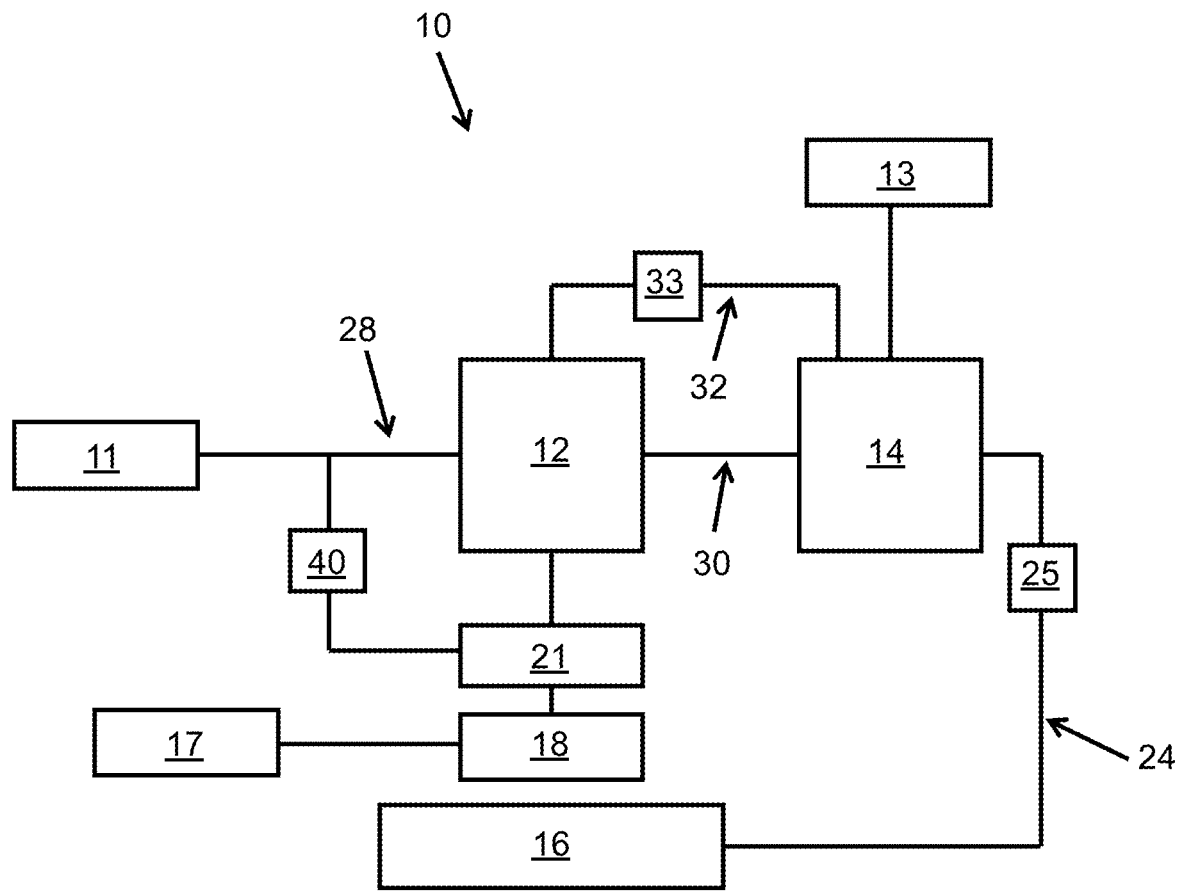
FIG. 2 shows a schematic of a system used to generate hydrogen in accordance with another embodiment of the disclosure.

In another embodiment, as best shown in FIG. 2, a water supply 21 is in fluid communication with photobioreactor 12 and photosynthesis heat exchanger 18 is in thermal communication with the water supply 21. This arrangement means that heat provided to the photobioreactor 12 is passed to the biodecomposition reactor 14 by virtue of the passage of the organic feedstock from the photobioreactor 12 to the biodegradation reactor 14. However, the embodiment shown in FIG. 2 may also include biodecomposition heat exchanger 20. In the embodiment shown in FIG. 2, the water supply 21 can include a mist generator for generating a mist of water from the water supply. The photosynthesis heat exchanger 18 can be in thermal communication with the mist generator.

In a variation of the embodiment of FIG. 2, the water supply 21 is not in thermal communication with the heat exchanger 18 and instead the heat exchanger 18 is only in thermal communication with the photobioreactor 12.

The water supply 21 can have two water supply channels, one leading directly to the photobioreactor 12 and another leading to a carbon dioxide mixing chamber 40. The carbon dioxide mixing chamber 40 receives carbon dioxide e.g.

from carbon dioxide supply line 28 to form a carbon dioxide-enriched solution that is then delivered to the photobioreactor 12. In an embodiment the mixing chamber 40 forms an emulsion of carbon dioxide and water.

Generally, the heat exchangers 18 and 20 will heat their respective reactors to maintain the reactors at required temperatures. Typically, the reactors 12 and 14 are maintained at a temperature ranging from about 30° C. to about 40° C. However, if reactor 12 and/or 14 includes extremophiles, the operational temperature may be in excess of 40° C., such as greater than 80° C. It should also be appreciated that the heat exchangers 18 and 20 may also be operated to cool their respective reactors. Alternatively, or additionally, photobioreactor 12 may be in thermal communication with biodecomposition reactor 14 to transfer heat between the reactors 12 and 14, for example if one reactor requires constant cooling and the other reactor requires constant heating.

Figure 3:
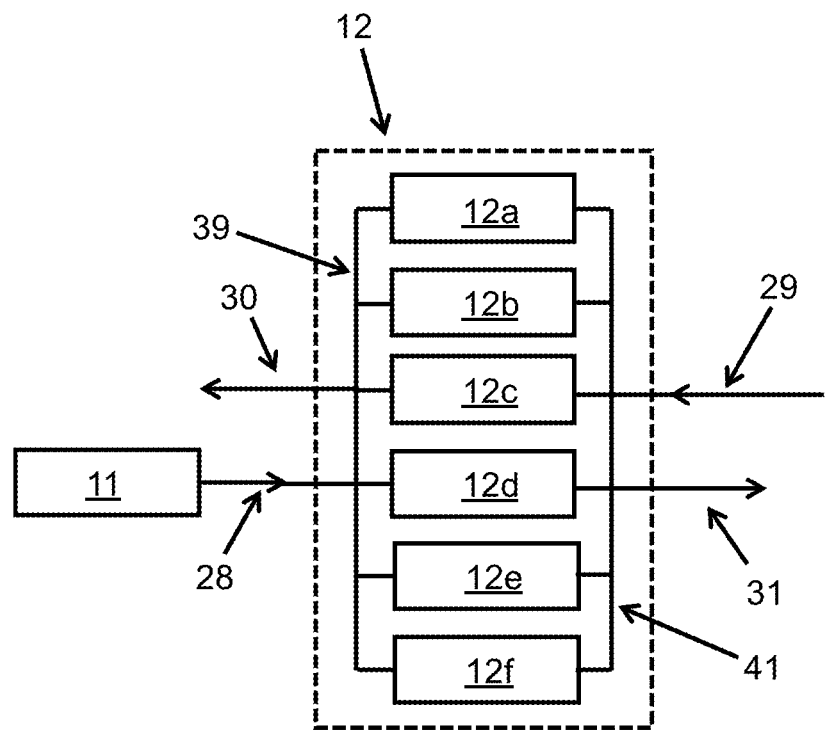
FIG. 3 shows a schematic of an embodiment of a photosynthesis reactor.

The photobioreactor 12 and biodecomposition reactor 14 are each depicted in FIGS. 1 and 2 as a single reactor but, in an embodiment, the photobioreactor 12 and/or biodecomposition reactor 14 may include a plurality of reactors. For example, FIG. 3 shows an embodiment of the photobioreactor 12 having six reactors 12a-12f. The reactors 12a-12f are connected in parallel. A gas manifold 39 connects the carbon dioxide supply line 28 to the reactors 12a-12f. An algal manifold 41 connects an algal supply line 29 to the reactors 12a-12f. The reactors 12a-12f are arranged for counter current flow of carbon dioxide and algal material. In a variation to the embodiment of FIG. 3, the reactors 12a-12f are connected in series.

An outlet gas line 31 is provided to allow excess gas(es) to be removed from the reactors 12a-12f. If the excess gases include carbon dioxide, the excess gases can be reintroduced into carbon dioxide supply line 28. When the reactors 12a-12f are connected in series, the carbon dioxide and algal flow may be co-current or counter-current. FIG. 3 is exemplary only and the embodiments for the photobioreactor 12 that include a plurality of reactors can also apply to the biodecomposition reactor 14. In an embodiment, each of the plurality of reactors are modular units. To increase an output of the system 10, additional modular units can be added to the respective reactor. Another advantage of modular reactor units is that one unit can be taken offline, for example for maintenance, without the system 10 having to be shut down entirely. In an embodiment, the photobioreactor 12 has six modular reactors and biodecomposition reactor 14 has six modular reactors.

Figure 5:
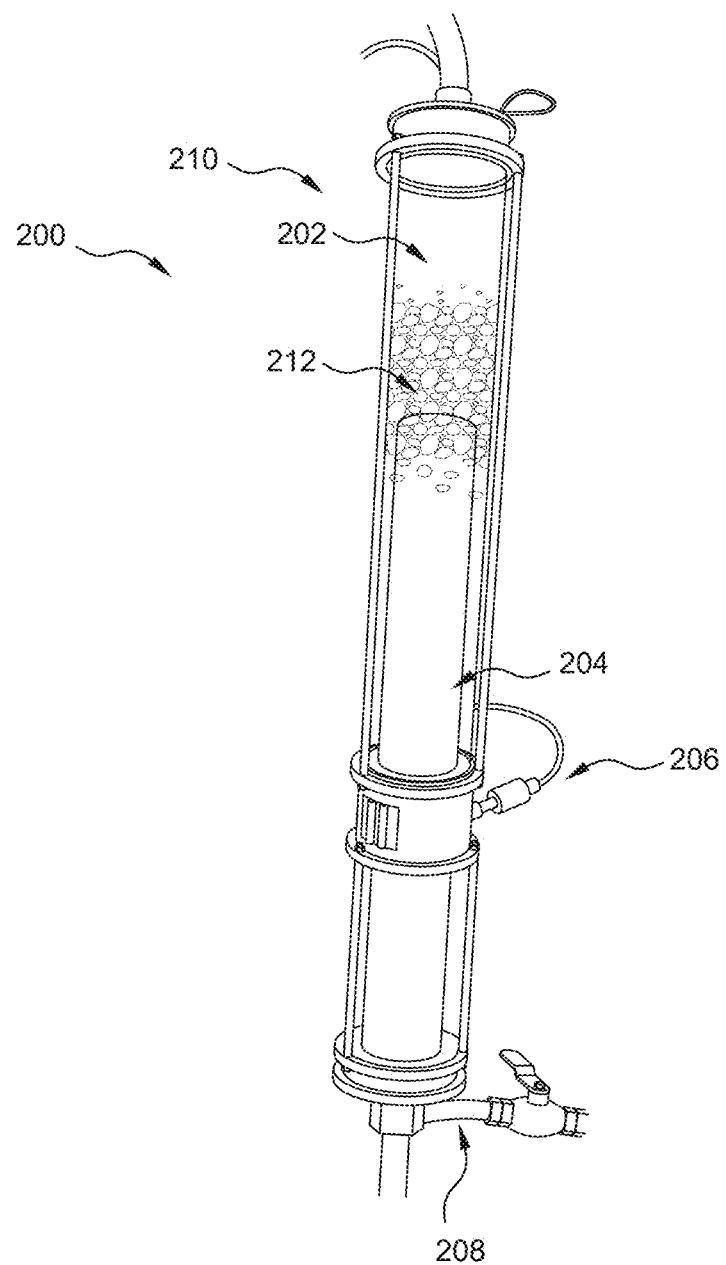
FIG. 5 shows an embodiment of a photosynthesis reactor.

An example of a modular biophotoreactor (i.e. photosynthesis reactor) is shown in FIG. 5. The modular biophotoreactor 200 is a hollow tube 202 fitted with a light source in the form of lamp 204 in an internal space of the tube 202. The reactor 200 has a capacity of about 1,200 L. A power source 206 is connected to the lamp 204. The reactor 200 can have a plurality of lamps 204. The lamp 204 may emit visible and/or UV light. The hollow tube 202 in use is filled with reaction media 212 that includes an algal source. The reactor 200 has a gas inlet 208 fitted near an in-use bottom end of the hollow tube 202. The gas inlet 208 is used to pass carbon dioxide into the hollow tube 202. Input line 210 is positioned near an in-use top end of the hollow tube 202. Input line 210 is used to add algal sources, reaction media, buffers, pH adjusters and so on to the hollow tube 202. The reactor 200 also has an outlet (not shown) for extracting the organic feedstock generated by the photosynthetic conversion of carbon dioxide. The lamp 204 can be powered using renewable energy.

In one embodiment, the system 10 is provided with photovoltaic elements and an associated battery system that may be used to power the light source 204. In a variation, the light source is omitted, and sunlight is used as the light source. In another variation, sunlight is used as the light source during daylight hours and the lamp 204 is used as the light source during night to allow the photobioreactor to operate continuously.

Returning to FIGS. 1 and 2, the biodecomposition reactor 14 is connected to an air supply 13. In an embodiment the air supply is a compressor. The air supply 13 can be fitted with a biological filter for filtering out biological material from the air supplied. The air supplied by the air supply 13 to the biodecomposition reactor 14 assists the bacterial-derived conversion to hydrogen gas of the organic feedstock produced by the photobioreactor 12.

During the photosynthesis step in the photobioreactor 12 and biodecomposition step in the biodecomposition reactor 14, there may be a build-up of dissolved organic matter. Dissolved organic matter has the potential to act as a surfactant and create foam. The production of foam in each reactor 12 and 14 can reduce the ability of the system 10 to convert carbon dioxide into hydrogen. To combat this, in an embodiment (not shown in the Figures), each of the photobioreactor 12 and biodecomposition reactor 14 also includes an antifoamer that is configured to prevent foam build up in the reactors 12 and 14.

In an embodiment the photobioreactor 12 and the biodecomposition reactor 14 each includes numerous sensors including pH sensors, temperature sensors, reactor level sensors, and sensors to monitor feedstock generation from the photobioreactor 12 and gas generation from the biodecomposition reactor 14. In an embodiment the reactors 12 and 14 are fitted with rotameters to monitor the gas inflow into the reactors. The system 10 also includes a control system (not shown in Figures) that receives information from the various sensors. The control system can adjust parameters such as, for example, reactor temperature, algal and bacteria loading rates and pH to optimise the reaction conditions to allow the most efficient generation of hydrogen. Generally, each of the supply lines, such as auxiliary carbon dioxide supply line 32 and conduits 28, 30 and 24, are fitted with valves that are actionable and controllable by the control system to control the flow of the various components around the system 10. The control system can also include a datalogger.

Figure 11:
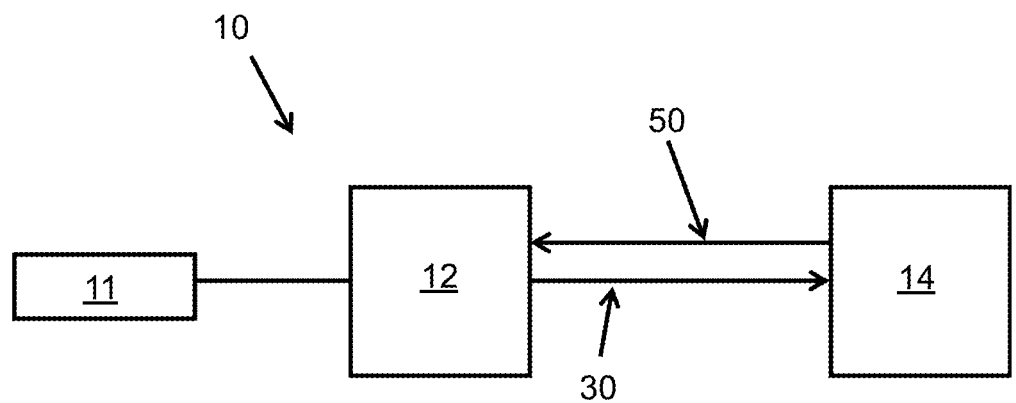
FIG. 11 shows a schematic of a system used to generate hydrogen in accordance with another embodiment of the disclosure.

FIG. 11 shows an embodiment in which a return line 50 connects the photobioreactor 12 and biodecomposition reactor 14. Return line 50 allows at least a portion of a product in the biodecomposition reactor 14 to be transferred (i.e. recirculated) back to the photobioreactor 12. Subjecting the product in the biodecomposition reactor 14 to further algal treatment in the photobioreactor 12 may help to improve the conversion of carbon dioxide into hydrogen by making more of the organic feedstock available to conversion to hydrogen through the organism processes of system 10.

Figure 12:
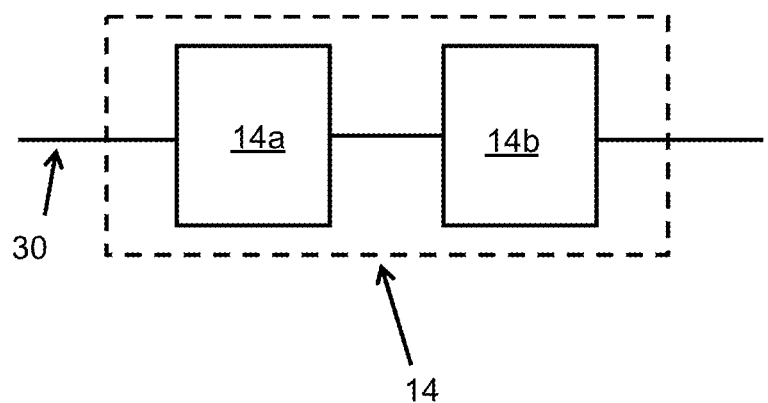
FIG. 12 shows a schematic of an embodiment of a biodecomposition reactor.

The biodecomposition reactor 14 in an embodiment has more than one reactor. As best seen in FIG. 12, an embodiment of the biodecomposition reactor 14 has a first reactor 14a and a second reactor 14b. Each of the reactors 14a and 14b can have different reactor conditions. For example, reactors 14a and 14b can have different bacterial species to perform first and second biodegradation processes. In an embodiment, one of the reactors 14a and 14b is an aerobic reactor and the other is an anaerobic reactor. In an embodiment, reactor 14a is an aerobic reactor and reactor 14b is an anaerobic reactor. When two or more biodecomposition reactors are used, the reaction conditions in each reactor may be operated independent from one another.

The return line 50 can also be used when two or more biodecomposition reactors are used. For example, the return line 50 can be connected to reactor 14a and/or 14b. In an embodiment, the return line 50 connects an aerobic reactor (e.g. 14a) and the photosynthetic reactor 12. Such an arrangement can be considered as a collective 'feed production stage' for the anaerobic biodecomposition step. When an aerobic reactor is used, an air supply (e.g. 13) can be fitted to the reactor to provide a supply of air. In an embodiment, the aerobic reactor 14a is operated for 24 hours and the anaerobic reactor 14b is operated for 48 hours.

Although two reactors 14a and 14b are shown in FIG. 12, in an embodiment a single reactor can be used to perform different biodecomposition processes. For example, in an embodiment, a single reactor can be set up so that aerobic biodecomposition is performed first then the reactor conditions are changed (e.g. oxygen/air evacuated) to perform anaerobic biodecomposition, or vice versa.

An advantage of system 10 is that it can be used to remove carbon dioxide emissions from industrial processes, such as emissions from the liquification of natural gas, and can produce hydrogen. Production of hydrogen whilst consuming carbon dioxide, rather than sequestering carbon dioxide, may help to eliminate the need for geological formations required for carbon dioxide sequestration. Further, the system 10 can be scaled up or down as required depending on the amount of carbon dioxide required to be processed, whereas carbon dioxide sequestration is often only viable for large quantities of carbon dioxide.

Figure 4:
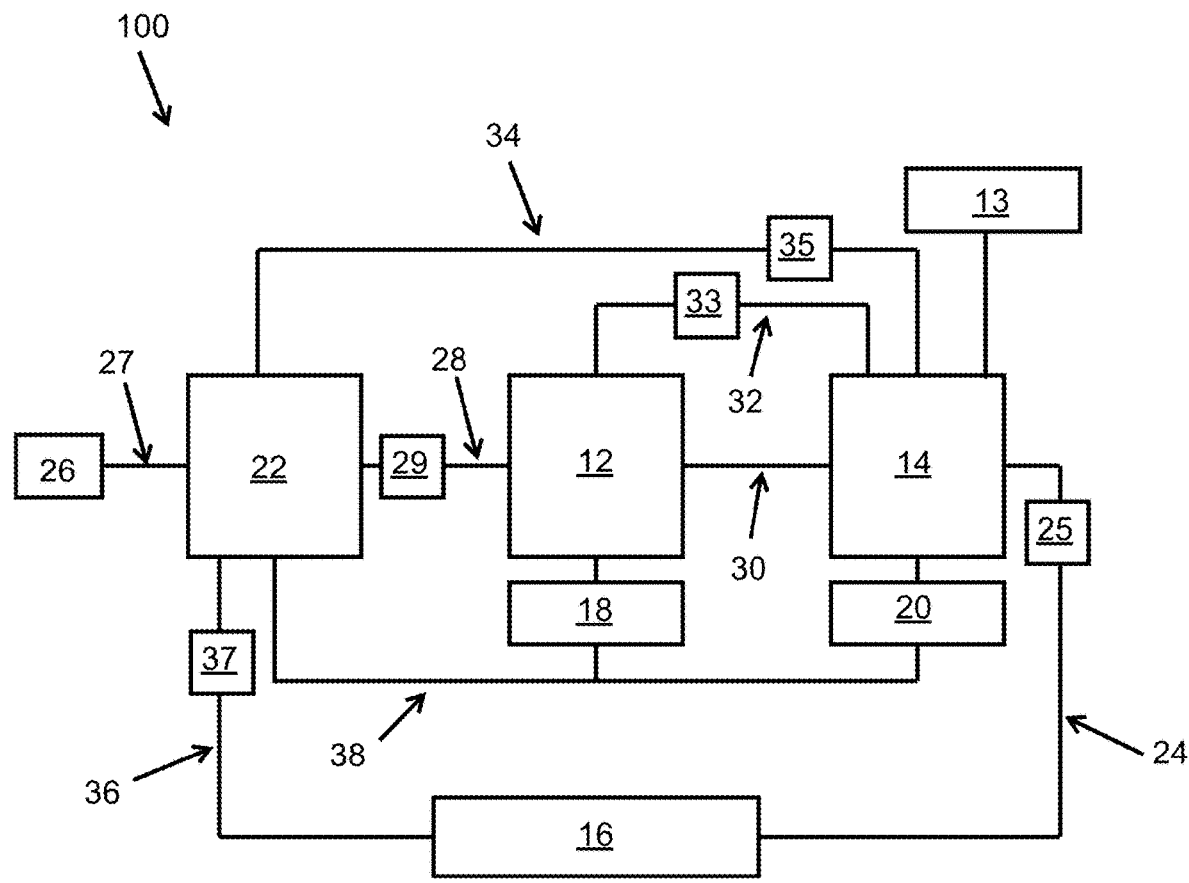
FIG. 4 shows a schematic of a system used to generate hydrogen in accordance with another embodiment of the disclosure.

Another embodiment of a system 100 is shown in FIG. 4. System 100 is similar to system 10 except that the carbon dioxide source 11 is a waste carbon dioxide gas stream generated from a gas reformer 22. Gas reformer 22 converts a hydrocarbon source 26, such as methane or plumbed natural gas, into hydrogen via steam reforming. A by-product of steam reforming is carbon dioxide. In the embodiment of FIG. 4, the carbon dioxide by-product is collected and passed from the gas reformer 22 through carbon dioxide supply line 28 to the photobioreactor 12. To separate the carbon dioxide in supply 28 from other gases generated by the gas reformer 22, such as carbon monoxide, steam and hydrogen, gas filter 29 may be provided on carbon dioxide supply line 28.

The hydrogen produced by the gas reformer 22 is collected and passed into storage vessel 16 via conduit 36. Conduit 36 may be provided with filter 37 to remove any contaminants from the hydrogen gas stream. In an embodiment, the biodecomposition reactor 14 also produces hydrocarbons when the organic feedstock from the photobioreactor 12 is converted into hydrogen. An auxiliary hydrocarbon feed line 34 connects the biodecomposition reactor 14 with the gas reformer 22 for passing hydrocarbon generated by the biodecomposition reactor 14 to the gas reformer 22. In an embodiment, the auxiliary hydrocarbon supply line 34 is fitted with a filter 35 for purifying the hydrocarbons generated by the biodecomposition reactor 14 prior to delivery to the reformer 22.

Supplying the gas reformer 22 with hydrocarbons generated from the biodecomposition reactor 14, and also supplying the photobioreactor 12 with carbon dioxide generated from the biodecomposition reactor 14, may help to increase the amount of hydrogen generated per unit of hydrocarbon (e.g. source 26) from about 40% to about 65%, representing about a 63% increase in the amount of hydrogen generated.

Figure 6:
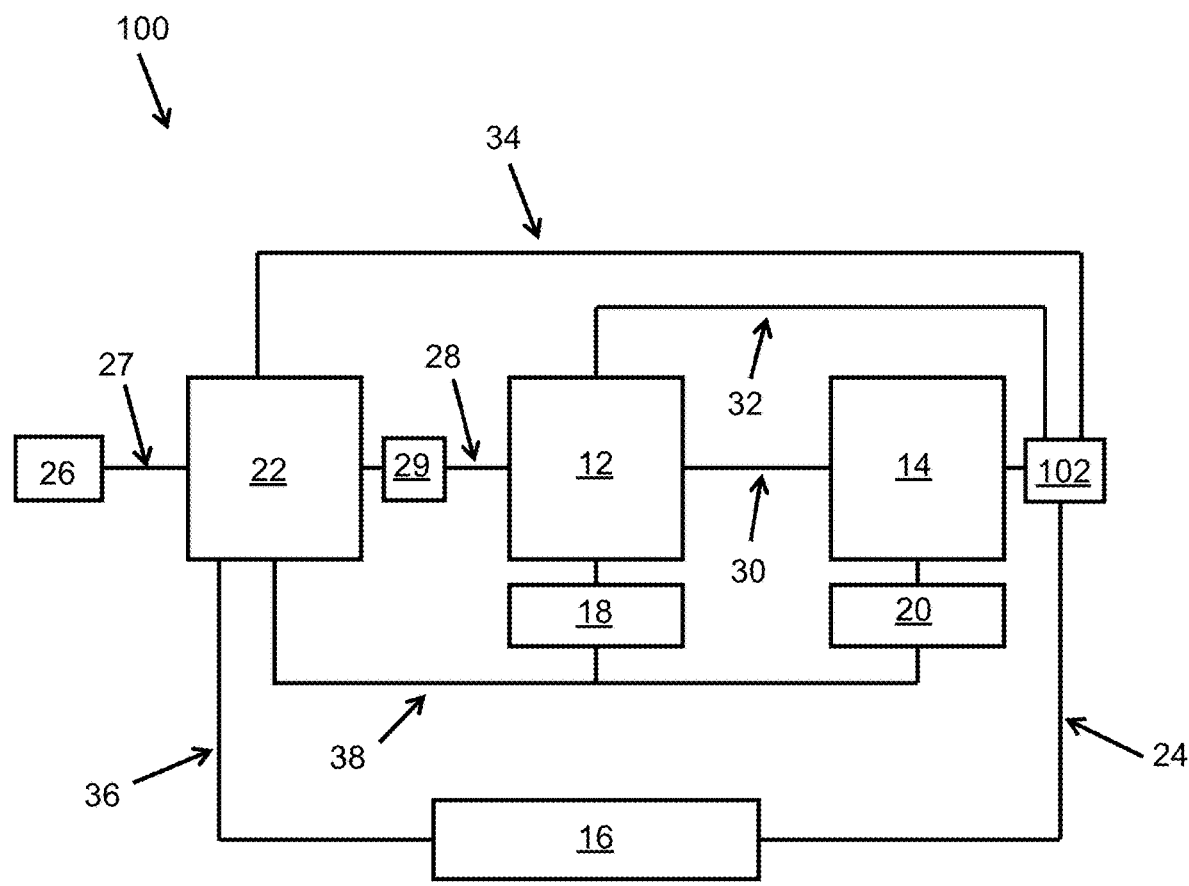
FIG. 6 shows a schematic of a system used to generate hydrogen in accordance with another embodiment of the disclosure.

In an embodiment, supply lines 32 and 34, and conduit 24, are connected to a manifold 102 as shown in FIG. 6. Manifold 102 is connected to a gas outlet of biodecomposition reactor 14. Manifold 102 is also fitted with a filter so that the hydrogen, carbon dioxide and any hydrocarbons generated by the biodecomposition reactor 14 are filtered and passed in respective lines 24, 32 and 34. In the embodiments depicted in FIGS. 4 and 6, auxiliary hydrocarbon feed line 34 may alternatively join feed line 27 to form a single supply of hydrocarbons rather than having two hydrocarbon input lines into the reformer 22.

The gas reformer 22 is in thermal communication with the heat exchangers 18 and 20 (line 38) so that the heat generated by the gas reformer 22 is used to heat the reactors 12 and/or 14. Utilising the heat generated from the reformer 22 to heat the reactors 12 and 14 helps to reduce the energy requirements of reactors 12 and 14.

In an embodiment, the system 10 and/or 100 is provided with an extraction system for extracting the gas(es) generated in use of the system, such as hydrogen. The extraction system will generally be in communication with the biodecomposition reactor 14 to extract gases generated therein. The extraction system may apply a reduced pressure to cause outgassing of gases dissolved in the reaction media in the biodecomposition reactor 14.

In an embodiment, the system 10 and/or 100 is placed onto structures such as shipping containers. The structures may be portable structures. The structures may be modular. The different components of the system, such as photobioreactor 12 and biodecomposition reactor 14 may be provided on different structures so that each reactor is provided as its own modular unit. This means that the system 10 and/or 100 can be easily scaled up or down as required depending on the required hydrogen output by adding or subtracting the required modular units.

Figure 7:
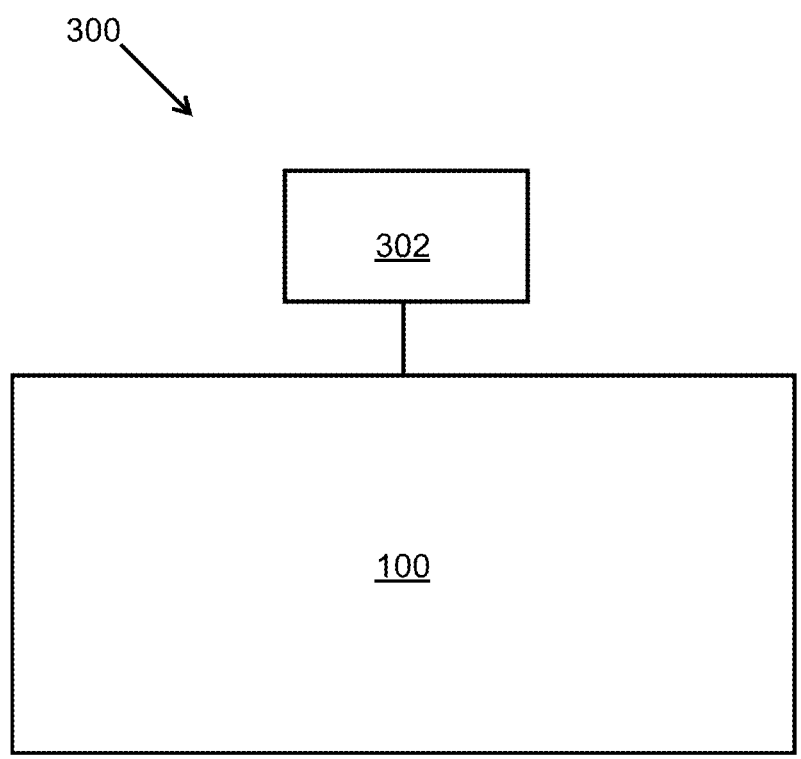
FIG. 7 shows a schematic of a system used to generate hydrogen in accordance with another embodiment of the disclosure.

A schematic of an embodiment of a process plant 300 for producing hydrogen is shown in FIG. 7 and is based on the system 100. The process plant 300 has a solar power generation system 302 that is used to provide power to system 100 to maintain a lower overall demand for grid energy, and as a daylight fail-safe should grid energy be temporarily disrupted. In an embodiment, the process plant 300 fits within a footprint of two 20-foot sea containers. In another embodiment of plant 300, system 100 is replaced with system 10.

The system 100 (e.g. plant 300) can be utilised as a hydrogen vehicle refuelling station. Grid gas is available at most locations in populous areas and can be used as the gas source for the reformer 22. An advantage of using existing retail grid gas networks and infrastructure to generate hydrogen is that transportation of hydrogen to refuelling stations can be eliminated and the hydrogen can be generated on site in response to demand. The system 100 may also reduce the need to store large quantities of hydrogen to meet expected demand. The system 100 combines existing retail gas infrastructure with service station located bio-reactors to generate hydrogen. The use of the photobioreactor 12 and the biodecomposition reactor 14 to generate hydrogen from the carbon dioxide generated from the reformer 22 can allow a smaller reformer to be used, because the hydrogen output per unit of gas input into the system 100 is increased by about 65%. A smaller reformer reduces capital and operational costs and helps to reduce the cost of hydrogen.

Figure 8:
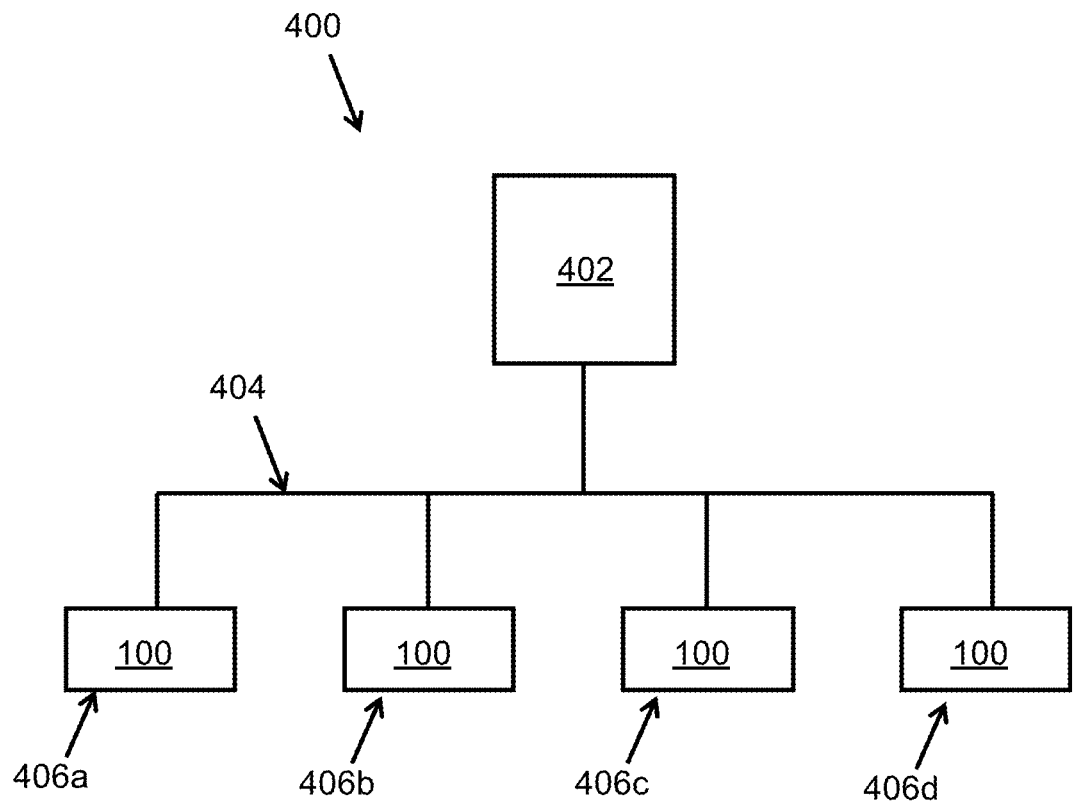
FIG. 8 shows a schematic of a distribution system used to generate hydrogen at separation locations relative a gas supply.

FIG. 8 shows an embodiment of a distribution system 400 for generating hydrogen at separate locations, such as hydrogen vehicle refuelling stations. System 400 has a grid gas supply 402 that is connected via gas networks and infrastructure 404 to a plurality of systems 100 at separate locations 406a-d. Each of the locations 406a-d can be a hydrogen vehicle refuelling station. Each system 100 may be optimised to generate hydrogen at each location 406a-d depending on the hydrogen requirements of each location 406a-d.

In an embodiment, the system 100 at each location 406a-d may have a capacity of about 14,400 L with an overall hydrogen output of about 500 kg/day. When the system 10 is used to capture carbon dioxide produced from a LNG plant, the system 10 may have a capacity of about 11,700,000 L with an overall hydrogen output of about 10,000 kg/day.

The embodiments described in the Figures show the photobioreactor 12 and the biodecomposition reactor 14 as separate reactors. However, in an embodiment, the photosynthetic conversion of carbon dioxide into the organic feedstock and the biodecomposition conversion of the organic feedstock into hydrogen can occur in the same reactor, so the photobioreactor 12 and the biodecomposition reactor 14 are one and the same unit.

An embodiment of the disclosed process may enable use of a high concentration of carbon dioxide (between 8%-20%) than in air (0.0314%) and can require much less water mass (hydrogen source) for a given mass of hydrogen output. Further, as reasonably predicted by the inventors, compared to any known technology today, an embodiment of the disclosed process may: produce up to 500-2,000 times more hydrogen per day for a given reactor vessel size; produce up to 28 times more hydrogen (kg) per kilogram of carbon dioxide consumed; consume up to 51 times more carbon dioxide (kg) per kilogram of hydrogen produced; and yield 13% of total available hydrogen within a biological system (vs 0.009%).

Figure 9:
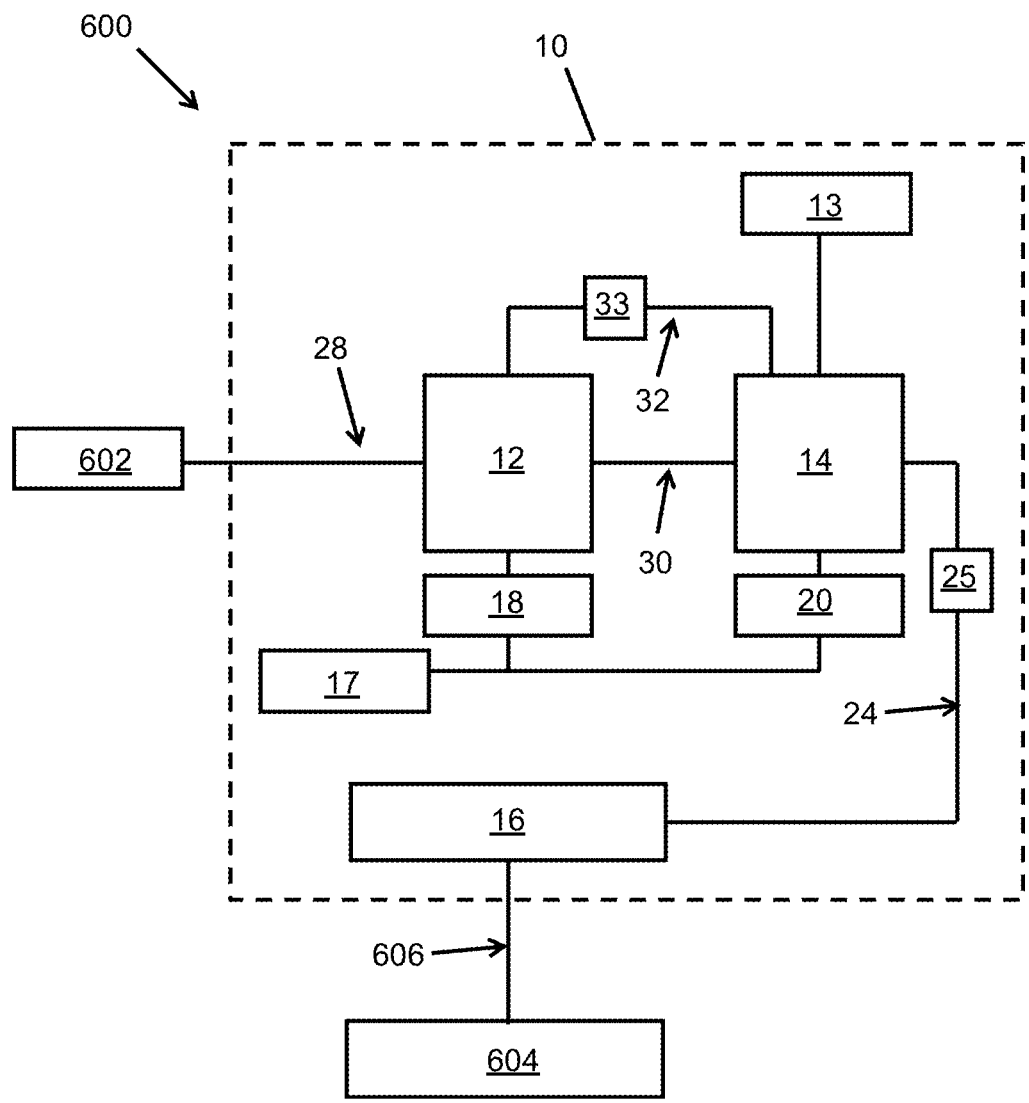
FIG. 9 shows a schematic of a system used to generate electricity in accordance with an embodiment of the disclosure.

FIG. 9 shows an embodiment of a system 600 used to generate electricity. System 600 has a coal-fired power station 602. Flue gas of the power station 602 includes carbon dioxide. The flue gas of the power station 602 is in fluid communication with the photobioreactor 12 from system 10 and acts as the first waste carbon dioxide gas stream. In an embodiment, a filter is provided between the power station 602 and the photobioreactor 12 to filter off gases other than carbon dioxide in the flue gas. System 10 converts the first waste carbon dioxide stream into hydrogen to be stored in vessel 16, as described above. In system 600, a hydrogen fuel cell 604 is connected to the vessel 16 by conduit 606. Hydrogen stored in the vessel 16 can be transferred through conduit 606 to the fuel cell 604 for the generation therein of electricity. In an embodiment, vessel 16 and conduit 606 are omitted and hydrogen produced in the biodecomposition reactor 14 is passed directly through conduit 24 to the fuel cell 604. Electricity produced by the fuel cell 604 can be fed into the power station 602 for distribution or can be distributed independently of the power generated by the power station 602. By utilising carbon dioxide present in flue gas from a power station as a fuel source, system 600 may help to extract more energy from a unit of coal input into the power station 602. System 600 may also help to reduce the amount of carbon dioxide emitted from a coal-fired power station.

Figure 10:
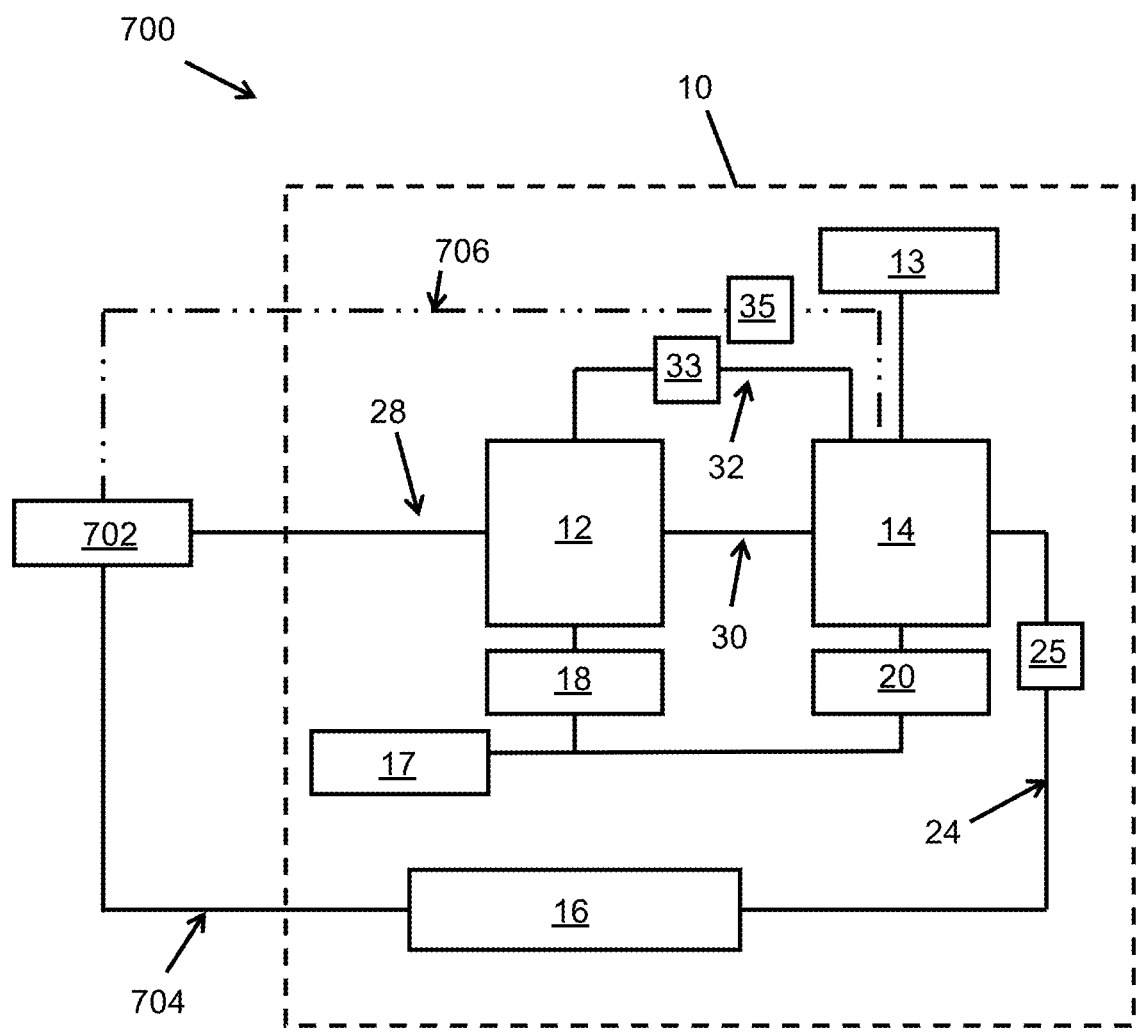
FIG. 10 shows a schematic of a system used to generate electricity in accordance with another embodiment of the disclosure.

FIG. 10 shows another embodiment of a system 700 used to generate electricity. System 700 includes a gas-fired power station 702. The gas-fired power station may operate on hydrocarbons such as natural gas. Flue gas of the power station 702 includes carbon dioxide. The flue gas of the power station 702 is in fluid communication with the photobioreactor 12 from system 10 and acts as the first waste carbon dioxide gas stream. In an embodiment a filter is provided between the power station 702 and the photobioreactor 12 to filter off gases other than carbon dioxide. System 10 converts the first waste carbon dioxide stream into hydrogen to be stored in vessel 16, as described above. The vessel 16 is connected to the power station 702 by conduit 704. Conduit 704 allows hydrogen stored in the vessel 16 to be transferred to the power station 702 where the hydrogen gas can be mixed with hydrocarbon gas to form a hydrogen-enriched gas that is combusted in the power station 702. System 700 may also be optionally fitted with auxiliary hydrocarbon supply line 706. Any hydrocarbons produced in the biodecomposition reactor 14, such as methane, can be transferred through conduit 706 to the power station 702 and mixed with the natural gas that is combusted in the power station 702. The hydrogen and optionally hydrocarbons produced by the system 10 are used to supplement the primary gas input that is combusted in the power plant 702. By utilising carbon dioxide in flue gas from a power station as a fuel source, system 700 may help to extract more energy from a unit of gas input into the power station 702. System 700 may also help to reduce the amount of carbon dioxide emitted from a gas-fired power station.

EXAMPLES

Embodiments will now be described using non-limiting Examples.

Example 1

An embodiment of a lab test is as follows.

A 120 L solution of culture medium and 5 litres of inoculum of the *Chlorella vulgaris* species with air and $CO_2$ injection at a flow rate of 0.5 to 1.0 VVM were processed for a period of 4 days inside the photosynthesis reactor until the reactor had a biomass refraction sufficient for circulation and removal. The photobioreactor was fitted with two 12 V LEDs with blue and red wavelength of 400-1500-1800 $\mu Em^{-2}s^{-1}$.

Part of the biomass (60%) produced in the photosynthesis reactor was transferred to the biodecomposition reactor for digestion of the biomass (e.g. sugars) into gas including hydrogen. The remaining 40% of the biomass was stored for use as an inoculum of the photosynthetic reactor or as a biofertilizer feedstock.

In the biodecomposition reactor, the biomass was inserted in an aerobic regime, together with 15 liters of inoculum in a concentration of $2 \times 10^{11}$ (cells per ml) of *B. subtilis* in the bioreactor, with the insertion of atmospheric gases at 0.8 VVM for 48 hours, after which time the biodecomposition reactor was transferred to an anaerobic regime with Anaerobic bacteria *A. aerogenes* (currently classified as *K. aerogenes*) in the concentration $1.5 \times 10^{10}$ (cells per ml).

The biomass in the biodecomposition reactor was digested for 48 hours forming gases that were removed by an exhaust system and separated by filtration into their respective components (e.g. a $CO_2$ stream, $H_2$ stream, $CH_4$ stream), which were recirculated or removed and stored depending on the requirement of the system used to produce the $H_2$. After digestion, the liquid containing digested nutrients, bacteria and water were reused as an inoculum of the system or as a biofertilizer soil conditioner.

Example 2

A 120 L solution of culture medium and 5 litres of inoculum of the *Chlorella vulgaris* species with air and $CO_2$ injection at a flow rate of 0.2 to 0.8 VVM were used for a period of 48 hours inside the photosynthesis reactor until the reactor had a biomass refraction sufficient for circulation and removal. A concentration of the carbon dioxide ranged from 8-20 vol %. The photobioreactor was fitted with two 12 V LEDs with blue and red wavelength of 400-1500-1800 $\mu Em^{-2}s^{-1}$.

Part of the biomass (60%) produced in the photosynthesis reactor was transferred to the biodecomposition reactor for digestion of the biomass (e.g. sugars) into gas including hydrogen. The biomass transferred to the biodecomposition reactor had a carbohydrate yield of about 78%, being made of up of approximately 35% glucose equivalents and galactose variants. The remaining 40% of the biomass was stored for use as an inoculum of the photosynthetic reactor or as a biofertilizer feedstock.

In the biodecomposition reactor, the biomass was inserted in an aerobic regime, together with 15 liters of inoculum in the concentration of $2\times10^{11}$ (cells per ml) of *B. subtilis* in the bioreactor, with the insertion of atmospheric gases at 0.8 VVM for 24 hours, after which time the biodecomposition reactor was transferred to an anaerobic regime with Anaerobic bacteria *A. aerogenes* (now called *K. aerogenes*) in a concentration $1.5\times10^{10}$ (cells per ml) for 48 hours.

Example 3

Example 2 was repeated, but 8010 L of culture medium and 335 L of *Chlorella vulgaris* was incubated in the photosynthetic reactor for 48 hours. 60% of the biomass produced in the photobioreactor was transferred to an aerobic biodecomposition reactor with 1000 L of *B. subtilis* where it was incubated for 24 hours. Following aerobic biodegradation, anaerobic biodegradation with *A. aerogenes* (currently classified as *K. aerogenes*) was performed to produce 81 kg/day of hydrogen gas, 513 kg/day carbon dioxide, 596 kg/day methane.

It will be understood to persons skilled in the art that many modifications may be made to the above described embodiments without departing from the spirit and scope of the disclosure. The embodiments described above are exemplary only and are not intended to limit the scope of the disclosure.

In the claims which follow and in the preceding description, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments.

What is claimed is:

1. A process for generating a hydrogen gas stream from a carbon dioxide gas stream, the process comprising:
   (i) converting a first waste carbon dioxide gas stream to an organic feedstock using an algal source in a photosynthesis step; and
   (ii) subjecting the organic feedstock to biodecomposition, said biodecomposition converting to a first hydrogen gas stream and gaseous by-products, the biodecomposition having sequential steps using bacteria to biodecompose the organic feedstock, said sequential steps comprising:
   as a first step of the sequential steps, an aerobic biodecomposition step subjecting the organic feedstock to aerobic biodecomposition using an aerobic bacteria to produce a first biodecomposition product; and
   an anaerobic biodecomposition step using an anaerobic bacteria to biodecompose the first biodecomposition product to produce the first hydrogen gas stream;
   wherein the aerobic bacteria and the anaerobic bacteria are different species.

2. The process as claimed in claim 1, further comprising collecting the gaseous by-products from step (ii) and filtering the gaseous by-products to isolate a second waste carbon dioxide gas stream; and optionally transferring the second waste carbon dioxide gas stream to step (i).

3. The process as claimed in claim 1, wherein step (i) is performed in a microbial reactor that is fitted with a photon source.

4. The process as claimed in claim 1, wherein at least a portion of a product of the aerobic biodecomposition step is mixed with the algal source in step (i) prior to the anaerobic biodecomposition step.

5. The process as claimed in claim 1, wherein step (ii) is performed in one or more biodecomposition reactors, with step (i) and step (ii) optionally able to occur in a same reactor.

6. The process as claimed in claim 1, wherein the first waste carbon dioxide gas stream is generated from a gas reformer that forms a secondary hydrogen gas stream from a hydrocarbon source, the first hydrogen gas stream produced by the anaerobic biodecomposition step optionally supplementing the secondary hydrogen gas stream produced by the gas reformer.

7. The process as claimed in claim 6, wherein heat is generated from the gas reformer and a temperature of step (i) and/or (ii) is regulated by utilising at least some of the heat generated from the gas reformer.

8. The process as claimed in claim 6, wherein the hydrocarbon source is natural gas.

9. The process as claimed in claim 1, further comprising collecting a biomass waste stream generated in step (i) and/or (ii).

10. The process as claimed in claim 1, wherein the aerobic biodecomposition step uses a bacterial species of the Bacilli class to biodecompose the organic feedstock to produce the first biodecomposition product, and the anaerobic biodecomposition step uses a bacterial species of the Gammaproteobacteria class to biodecompose the first biodecomposition product to produce the first hydrogen gas stream.

11. The process as claimed in claim 10, wherein the algal source comprises a species of the *Chlorella* genus.

12. The process as claimed in claim 10, wherein the aerobic bacteria used for the aerobic biodecomposition step comprises a species of the *Bacillus* genus.

13. The process as claimed in claim 10, wherein the anaerobic bacteria used for the anaerobic biodecomposition step comprises a species of the *Klebsiella* genus.

14. A process for generating a hydrogen gas stream from a carbon dioxide gas stream, the process comprising:
   (i) mixing a first waste carbon dioxide gas stream and an algal source to form an organic feedstock;
   (ii) treating the organic feedstock in a first biodecomposition step to produce a first biodecomposition product; said first biodecomposition step being an aerobic biodecomposition step using aerobic bacterial species; and
   (iii) treating the first biodecomposition product in a sequential second biodecomposition step to produce hydrogen gas, said second biodecomposition step being an anaerobic biodecomposition step using anaerobic bacterial species;

wherein, prior to step (iii), at least a portion of the first biodecomposition product is mixed with the algal source in step (i)

wherein the aerobic bacterial species and the anaerobic bacterial species are different species.

15. The process as claimed in claim 14, wherein the first biodecomposition step is aerobic and the sequential second biodecomposition step is anaerobic.

16. A process for generating a hydrogen gas stream from a carbon dioxide gas stream, the process comprising:
   (i) converting a first waste carbon dioxide gas stream to an organic feedstock using an algal source in a photosynthesis step, said algal source the algal source comprises one or more algal species capable of photosynthesis; and
   (ii) subjecting the organic feedstock to biodecomposition, said biodecomposition converting to a first hydrogen gas stream and gaseous by-products, the biodecomposition having sequential steps using bacteria to biodecompose the organic feedstock, said sequential steps comprising:
   as a first step of the sequential steps, an aerobic biodecomposition step subjecting the organic feedstock to aerobic biodecomposition using an aerobic bacteria to produce a first biodecomposition product, said organic feedstock comprising viable cells of said one or more algal species; and
   an anaerobic biodecomposition step using an anaerobic bacteria to biodecompose the first biodecomposition product to produce the first hydrogen gas stream
   wherein the aerobic bacteria and the anaerobic bacteria are different species.

* * * * *